United States Patent

Schiek, Sr. et al.

[11] Patent Number: 5,086,758
[45] Date of Patent: Feb. 11, 1992

[54] BELT SUPPORT DEVICE WITH ADJUSTABLE HOOK AND LOOP-TYPE FASTENER

[76] Inventors: James W. Schiek, Sr., 513 B Saratoga Ave., Fond du Lac, Wis. 54935; James M. Schiek, 1031 S. Webster, Omro, Wis. 54963

[21] Appl. No.: 665,990

[22] Filed: Mar. 7, 1991

[51] Int. Cl.⁵ .................. A61F 5/02; A61F 5/37; A63B 21/072; A41F 3/02
[52] U.S. Cl. .................. 602/19; 128/876; 272/123; 272/143; 2/338
[58] Field of Search ....... 128/875, 876, 874, DIG. 15, 128/78, 24 R, 100.1, 101.1, 102.1, 112.1, 89 R; 24/31 V; 2/311, 312, 338, 339, DIG. 6; 272/143, 123

[56] References Cited

U.S. PATENT DOCUMENTS

| | | | |
|---|---|---|---|
| 2,914,070 | 11/1959 | Kellner | 2/311 |
| 3,374,636 | 3/1968 | Mason | 405/186 |
| 3,659,843 | 5/1972 | Kojigian, Jr. | 128/DIG. 15 |
| 3,888,245 | 6/1975 | Bernston et al. | 128/78 |
| 4,054,952 | 11/1977 | Swallow | 128/DIG. 15 |
| 4,085,746 | 4/1978 | Castiglia | 128/DIG. 15 |
| 4,414,969 | 11/1983 | Heyman | 128/DIG. 15 |
| 4,498,201 | 2/1985 | Carter | 2/311 |
| 4,621,619 | 11/1986 | Sharpe | 128/DIG. 15 |
| 4,864,698 | 9/1989 | Brame | 128/DIG. 15 |
| 4,911,432 | 9/1990 | Walden | 272/119 |
| 4,941,237 | 7/1990 | Hovis | 2/338 |
| 4,964,401 | 10/1990 | Taigen | 128/876 |

Primary Examiner—Robert A. Hafer
Assistant Examiner—Michael Brown
Attorney, Agent, or Firm—Andrus, Sceales, Starke & Sawall

[57] ABSTRACT

A belt or belt-type support device includes a pair of straps, each having one of a complementary pair of pads of a hook and loop-type fastener system. A removable shield is placed over the surface of one of the pads to preclude inadvertent, premature engagement of the hooked and looped surfaces when the belt is placed in position around the waist of the wearer. Once the belt is properly positioned, the shield may be removed to facilitate engagement of the hook and loop fastener system.

9 Claims, 2 Drawing Sheets

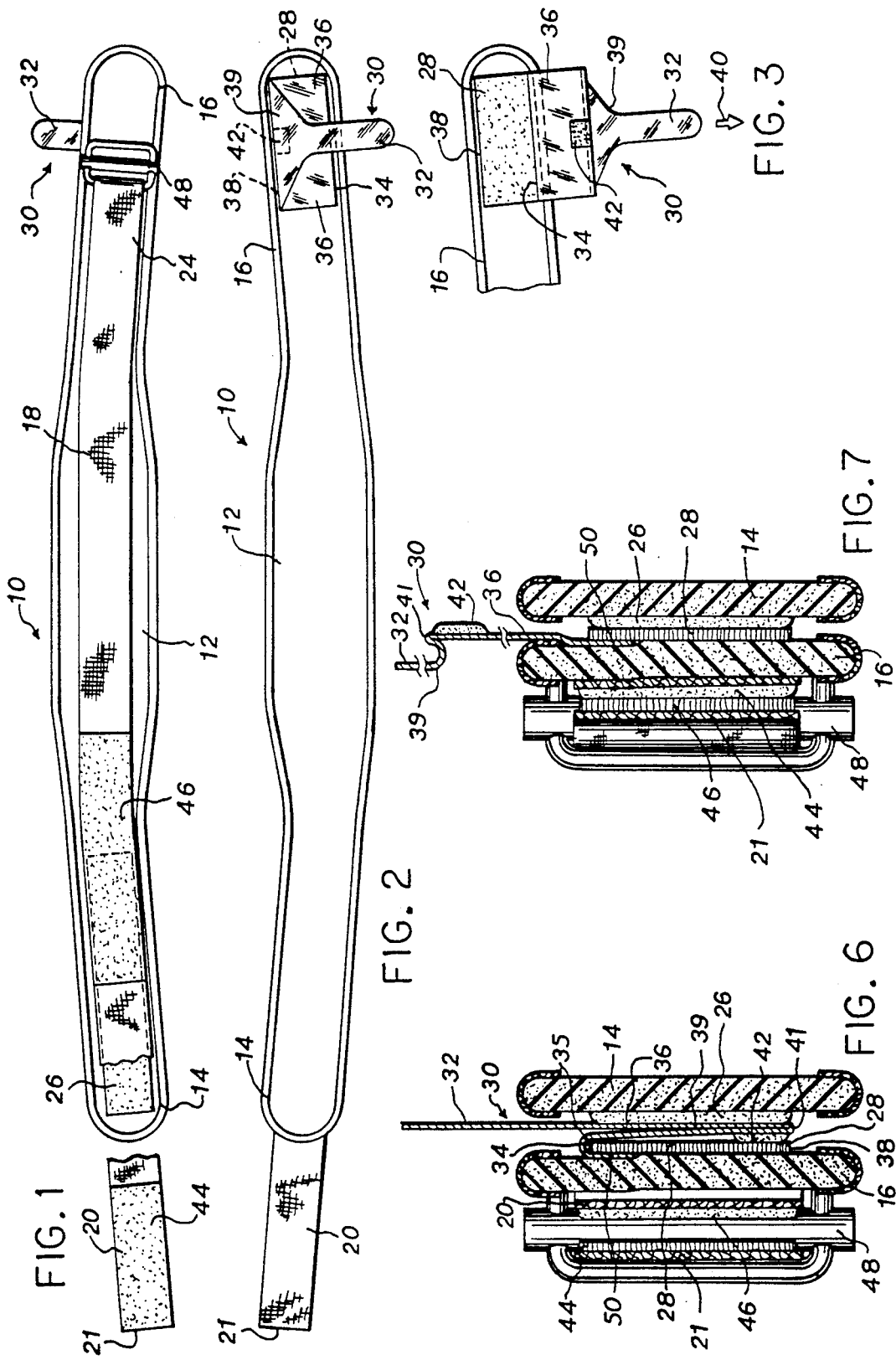

BELT SUPPORT DEVICE WITH ADJUSTABLE HOOK AND LOOP-TYPE FASTENER

BACKGROUND OF THE INVENTION

1. Field of the Invention

The subject invention is generally related to support devices and is specifically directed to a belt support having an adjustable hook and loop-type fastener.

2. Description of the Prior Art

This application is related to the co-pending application Ser. No. 07/491,349, James W. Schiek, Jr., Mar. 9, 1990 and our co-pending application Ser. No. 07/665,980, entitled "Adjustable Hook and Loop-Type Fastener Assembly", filed on even data herewith. The prior art includes a wide variety of support devices such as belts, braces, garments, and the like which are commonly used for therapeutic or orthopedic rehabilitation following injury or surgery. There are also many belts or support devices that are used by athletes and other sport enthusiasts during specific types of activities such as weight lifting, exercising and the like. Many of these devices are designed to encircle the wearer at the waist in the form of a belt to provide supportive or corrective force to the lumbar region and sacrum region of the back where injury is most likely to occur. Several of these devices use hook and loop-type reusable fastener systems to facilitate attachment of the belt or support device around the user.

Examples of belts and support assemblies using hook and loop-type fasteners are illustrated in U.S. Pat. No. 3,374,636 issued to D. F. Mason on Mar. 26, 1968; U.S. Pat. No. 3,659,843 issued on J. Kojigian, Jr. On May 2, 1972; U.S. Pat. No. 3,888,245 issued to E. B. Berston et al on June 10, 1975; U.S. Pat. No. 4,054,952 issued to R. Swallow On Oct. 25, 1977; U.S. Pat. No. 4,498,201 issued to R. S. Carter on Feb. 12, 1985; and U.S. Pat. No. 4,911,432 issued to D. Walden on Mar. 27, 1990.

Hook and loop-type fastener assemblies are well known. The Velcro brand fasteners have been available for many years. Other manufacturers produce products which function in basically the same manner as the Velcro brand hook and loop-type fastener. For example, 3M Corporation, Minneapolis, Minnesota, has several fastener systems which operate in the same basic manner as the hook and loop-type fastener. The 3M Dual Lock, the 3M Mushroom Loop, and the 3M Latchlok fastener systems are examples of fasteners which have the same function as the hook and loop-type fastener system originally developed by Velcro. Throughout this application when reference is made to the hook and loop-type fastener system, it is meant to encompass all the variations thereof.

All of these hook and loop-type fastener systems comprise a pair of complementary surfaces, generally available in strip or pad form. One of the strips or pads is provided with a hooked surface, and the mated strip or pad is provided with a looped surface. Once the complementary strips or pads are placed in mated juxtaposition and a light pressure is applied, they form a mechanical bond and provide a strong, semi-permanent closure which may be opened by removing, in sequence, a small portion of the hook and loop bond, preserving the system for reuse.

All of the hook and loop-type fasteners of the prior art have the same disadvantage in that once the two mated hooked and looped surfaces are placed in contact with one another, bonding is initiated. This precludes the adjustment or positioning of the two components which are to be fastened to one another after the components are placed in juxtaposition.

In many applications, it is desirable to reposition the components after they have been placed in juxtaposition, to assure proper placement and accuracy of assembly. In applications such as these, use of the typical hook and loop-type fastening system is impaired, if not rendered totally impractical.

SUMMARY OF THE INVENTION

The subject invention provides a support device or belt using a hook and loop-type fastener which is adjustable once the belt is in place and the mated hooked and looped surfaces of the fastener are placed in juxtaposition with one another. The fastener system includes a removable shield disposed between the mated, juxtaposed fastener surfaces to preclude inadvertent and premature engagement, permitting the belt to be adjusted and properly tensioned prior to engagement of the fastener members.

A flexible shield is provided over one of the hooked and looped surfaces and is permanently attached to the belt, with a pull tab extending outwardly from the belt when the belt or device is positioned around the waist of the wearer. Upon proper tensioning and placement of the belt by the wearer, the pull tab may be pulled, removing the shield from the fastener system, facilitating engagement and bonding of the fastener components. Once the belt is removed, the shield may be placed back over the surface of the fastener, for reuse.

In the preferred embodiment of the invention, the support belt includes dual strap systems, wherein a primary strap system is provided with the hook and loop-type fastener, when engaged and secured, provides a relatively immobile fastening system assuring that the tension on the belt is maintained constant during use. A secondary fastener system is designed to assist the wearer in tightening and initially tensioning the belt prior to activation of the primary fastener system. The primary fastener system includes a shield in combination with the hook and loop-type fastener assembly for precluding premature engagement and attachment of the primary fastener system while the belt is being tensioned by use of the secondary fastener system.

It is, therefore, an object and feature of the subject invention to provide for a belt or belt-type support device including a hook and loop-type fastener which is adjustable prior to engagement.

It is also an object and feature of the subject invention to provide for a belt or belt-type support device having a hook and loop-type fastener incorporating a removable shield between the hooked and looped surfaces of the fastener for precluding inadvertent and premature engagement of the fastener components during storage and use.

It is yet another object and feature of the subject invention to provide for a belt or belt-like support device having dual function fastening systems, wherein a tensioning fastener may be engaged and utilized in advance of a semi-permanent hook and loop-type fastener for securing the belt in place and assuring that constant tension is maintained during use, and wherein the semi-permanent fastener includes a hook and loop-type fastener assembly having a removable shield for protecting against inadvertent and premature engagement of the hook and loop-type fasteners.

Other objects and features of the invention will be readily apparent from the accompanying drawing and detailed description of the preferred embodiment.

BRIEF DESCRIPTION OF THE DRAWINGS

FIG. 1 is a front plan view of a belt in accordance with the subject invention.

FIG. 2 is a back plan view of the belt of FIG. 1.

FIG. 3 is a fragmentary view of the belt, as shown in FIG. 2, with the shield removed from the fastener surface.

FIG. 6 is a sectional view taken generally in the direction of arrows 6 of FIG. 4.

FIG. 7 is a sectional view taken generally in the direction of arrows 7 of FIG. 5.

DETAILED DESCRIPTION OF THE PREFERRED EMBODIMENT

Figure 4:
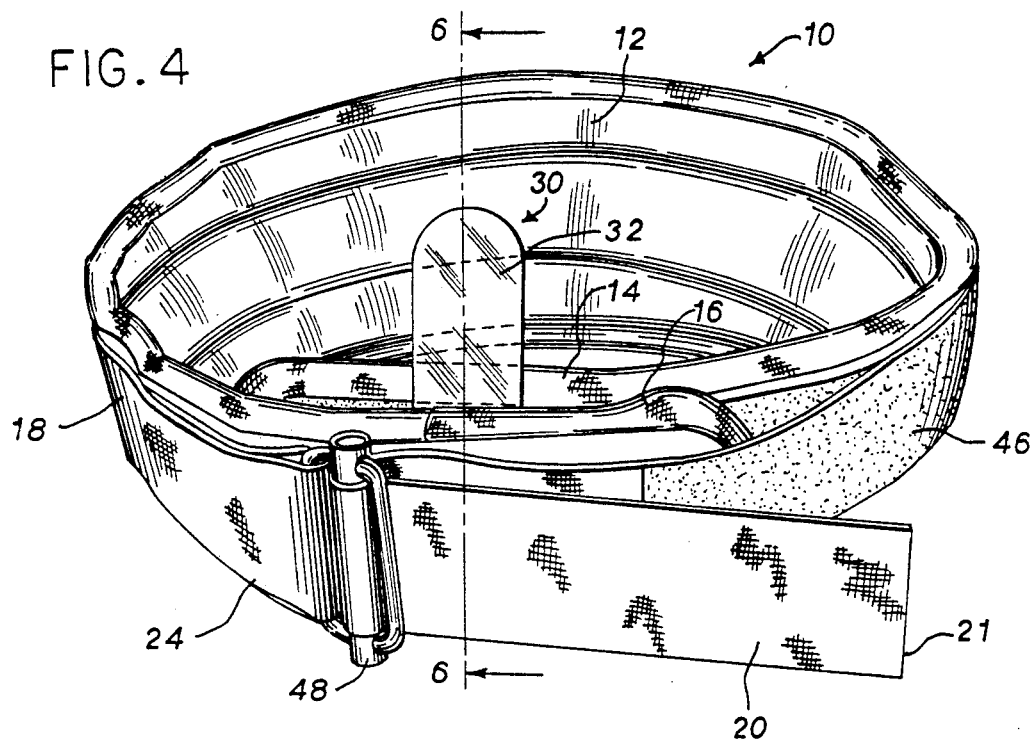
FIG. 4 is a perspective view of the belt, as assembled for use, with the shield in place.

As shown in FIG. 1, the belt 10 of the subject invention includes a back section 12 having attached thereto, and integral therewith, a pair of straps 14 and 16. A second elongate member 18 is attached to the back panel 12 of the belt and includes a second pair of straps 20, 24. As is shown in FIGS. 1 and 2, the first strap 14 includes a fastener pad 26 which is complementary with the fastener pad 28 provided on strap 16. The pads 26, 28 comprise the mated components of a typical hook and loop-type fastener system. When the belt is encircled about the waist of the user, the pads 26, 28 are placed in mated juxtaposition, and when slight pressure is applied a contact bond is completed in the well-known manner.

Since it is desirable to position the ends of the belt prior to securing the fasteners, a shield 30 is provided and covers pad 28 to preclude inadvertent, premature attachment. In the preferred embodiment and as particularly shown in FIG. 2, the shield 30 is attached directly to the belt adjacent the one edge 34 of the pad 28. A shield layer 36 extends over and spans the pad 28 and a fold line 38, adjacent the opposite edge of the pad 28, defines a flap 39 which terminates in the elongated tab 32.

When the tab 32 is pulled in the direction of arrow 40 (FIG. 3), the shield layer 36 is pulled back across pad 28, exposing the pad surface. In the preferred embodiment, the shield layer 36 includes a small patch or strip 42 which is the complementary fastener component to the pad 28. This holds the shield in place when the shield is positioned over the pad 28. The shield 30 is a flexible, durable material.

The belt of the preferred embodiment includes a secondary attachment means comprising the straps 20, 24. As specifically shown in FIG. 1, the strap 20 includes a hook and loop-type fastener pad 44 at its outer end and a mated pad 46 disposed on an interior section of the strap. The strap 24 includes a buckle or loop 48 secured in suitable manner to the outer end of strap 20.

In the preferred embodiment, the support device comprises a belt support adapted to encircle the waist area of the human body, and when tightened about the waist provides firm support to the lumbar region. Each of the straps 14, 16 extend obliquely from the back section with respect to the horizontal axis of the back section. The straps 20, 24 are parallel to the straps 14, 16. The oblique angle may range from about 4°-25° and is preferably about 15°. The taper provided by these angles define a frustoconical shape when the belt is secured about the waist of the wearer.

It will be readily understood that the fastener system may be used for any belt or strap assembly where adjustment after contact is desired. Straight straps, a unitary belt and other support devices using hook and loop-type fasteners will readily benefit from the subject invention.

The belt is more fully described in the copending application Ser. No. 07/491,349, entitled "Support Belt for the Lumbar Vertebrae", by James W. Schiek, Sr., one of the co-inventors of the subject application, and filed on Mar. 9, 1990. That application is incorporated by reference herein. As there described, the back 12 and straps 24, 26 are preferably of the integral, unitary construction formed of a pliable, non-elastic material. This type of structure is advantageous in that it eliminates the need of providing for individual fabric panels or sections that are joined at a seam as by stitching, which can be more costly, can produce a weak zone with use, and can cause and uncomfortable gathering or bunching at the seam. The back section is substantially rectangular, and has a vertical dimension or width that spans some or substantially all of the lumbar vertebrae, preferably all five lumbar vertebrae from the sacrum at the lower end of the spinal column to the 12th thoracic vertebra. The horizontal dimension or length of the back section is sufficient to span the lumbar region on each side of the spinal column, and more preferably to span part or all of the lateral lumbar region at the small of the back. Therefore, when the belt is drawn tightly about the waist, the back section is applied firmly to the lumbar vertebrae and back musculature. These dimensions will depend on the belt size, but for purposes of illustration, for an average belt, the horizontal dimension of the back is about 12–18 inches and the vertical dimension of the back section is about 3–6 inches. The straps 14, 16 are generally of smaller width than the back section, primarily to provide a more comfortable fit around the waist.

As best shown in FIGS. 6 and 7, the shield 30 is disposed between the hooked and looped surfaces of the pads 26, 28. In the preferred embodiment, the shield includes the strip 50 which is secured directly to one strap 16 of the belt, with the strip 28 disposed over the strip 50 and secured directly to the strap 16. The shield 30 is then folded along the line 35, as previously described to define a shield layer 36 which spans and completely covers the surface of the pad 28. A second fold 41 is provided adjacent to the opposite edge 38 of the pad 28 for defining the flap portion 39 of the shield 30. The flap portion 39 terminates in the tab 32.

Figure 5:
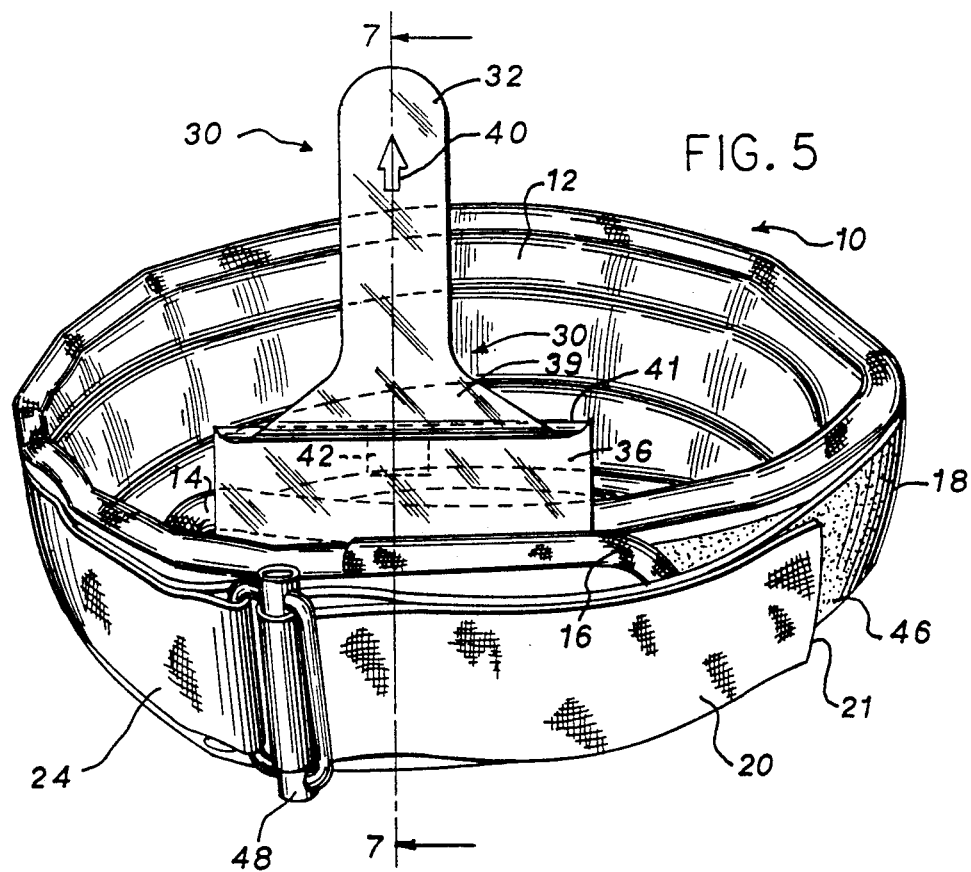
FIG. 5 is a view similar to FIG. 4, with the shield removed.

The second pair of straps 20, 24 are disposed outboard of the first pair of straps 14, 16. In use, the belt may be placed around the waist of the user with straps 14, 16 in place, with the shield 30 protecting against premature engagement of the pads 26, 28. The closure means 48, provided on strap 24 is then adapted for receiving the outer end 21 of the strap 20, whereby the belt may be tightened and tensioned to the satisfaction of the user. For convenience, the hook and loop-type fastener pad 46 may be provided on the surface of strap 20 and a mated hook and loop-type fastener pad 44 may be provided on the outer end 21 of the strap 20. The outer end 21 may then be secured to the belt by placing the mated surfaces 44, 46, in mated, engaged juxtaposition, as shown in FIG. 5. When the belt is properly positioned and tensioned, the tab 32 may be pulled in the direction of arrow 40, as shown in FIG. 7, for removing the shield layer 36 from interfering relationship with the mated adhesive pad surfaces 26, 28 and for permitting the mated surfaces of the pads 26, 28 to come into engagement and bond with one another, as shown in FIG. 7.

While certain features and embodiments of the invention have been described in detail herein, it will be readily understood that the invention encompasses all enhancements and modifications within the spirit and scope of the following claims.

What is claimed is:

1. In a support device of the type including a belt for adjustably encircling the human body about the waist, the device having a pair of straps extending laterally outward from the opposite sides thereof and having outer ends spaced outwardly therefrom, and improved means for securing the outer ends of said straps to one another and for adjusting the position of the straps relative to one another when the belt is first placed about the waist of a wearer, the improvement comprising:
   a. a first pad permanently secured to the outer end of one of said straps and including a hooked surface;
   b. a second pad permanently secured to the outer end of the other of said straps and including a looped surface, wherein the first and second pads may be secured to one another by placing the pads in mated juxtaposition, with the hooked and looped surfaces in contact with one another and by applying pressure to said pads; and
   c. a removable shield secured to the belt and removably placed over the surface of one of said pads for preventing inadvertent, premature engagement of the hooked and looped surfaces to one another, said shield being selectively removable from the pad surface when the belt is in use and replaceable over the pad surface during storage or for adjustment of the belt when first placed to encircle the waist of a wearer.

2. The improvement of claim 1, wherein said shield is an integral part of one of said pads.

3. The improvement of claim 1, further including a pull tab attached to said shield and accessible when said pads are placed in mated juxtaposition, whereby said tab may be pulled and said shield removed to permit engagement of the hooked and looped surfaces.

4. The improvement of claim 3, wherein in each of said pads includes opposite side edges and wherein said shield is secured to one of said side edges and spans the pad surface to the opposite side edge, and wherein said pull tab is secured to the shield adjacent said opposite side edge and extends back across said shield and pad surface beyond said one side edge.

5. The improvement of claim 1, wherein said shield is made of vinyl.

6. The improvement of claim 1, wherein the device further comprises a back section having vertical and horizontal axes and opposed sides laterally spaced along the horizontal axis, and a vertical dimension along the vertical axis spanning at least a portion of the lumbar vertebrae and adapted to bear upon the back musculature on both sides of at least one of said lumbar vertebrae, and wherein said straps extend laterally outward from the opposed sides of said back section, each of said straps extending along an axis forming an acute angle with respect to the horizontal axis of said back section, whereby said back section and straps define a tapered, truncated, conical belt.

7. In a support device for the lumbar vertebrae of the human spinal column, the support device of the type including an adjustable belt of a pliable, non-elastic material and adapted to encircle the waist area of the human body, and a pair of straps and means for adjustable encircling the human body about the waist, the device having a pair of straps extending laterally outward from the opposite sides thereof and having outer ends spaced outwardly therefrom, and improved means for securing the outer ends of said straps to one another and for adjusting the position of the straps relative to one another when the belt is first placed about the waist of a wearer, and a pair of straps and means for the support device comprising:
   a. a back section having vertical and horizontal axes and opposed sides laterally spaced along the horizontal axes and a vertical dimension along the vertical axis spanning at least a portion of the lumbar vertebrae and adapted to bear upon the back musculature on both sides of at least one of said lumbar vertebrae;
   b. first means including a pair of straps extending laterally outward from the opposed sides of said back section, each of said straps extending along an axis forming an acute angle with respect to horizontal axis of said back section and having outer ends spaced outwardly from said back section;
   c. a first pad secured to the outer end of one of said straps and including a hooked surface;
   d. a second pad secured to the outer end of the other of said straps and including a looped surface, wherein the first and second pads may be secured to one another by placing the pads in mated juxtaposition, with the hooked and looped surfaces in contact with one another and by applying pressure to said pads; and
   a removable shield secured to the belt and removably placed over the surface of one of said pads for preventing inadvertent, premature engagement of the hooked and looped surfaces to one another, said shield being selectively removable from the pad surface when the belt is in use and replaceable over the pad surface during storage or for adjustment of the belt when first placed to encircle the waist of a wearer.

8. The support device of claim 7, further including second means including a pair of straps extending outwardly from said back section, each along an axis substantially parallel to the axis of said first pair of straps, and closure means for securing and tightening said second straps for tightening the belt around the waist of the wearer for providing firm support, wherein said first strap means is adapted to be engaged after said second strap means by pulling said shield to engage the mated juxtaposed hooked and looped surfaces of said pads.

9. The support device of claim 8, wherein said first strap means and said back section are of integral construction.

* * * * *